United States Patent [19]

Yamamoto

[11] Patent Number: 5,776,671
[45] Date of Patent: Jul. 7, 1998

[54] DIAGNOSTIC AND PROGNOSTIC ELISA ASSAYS OF SERUM α-N-ACETYLGALACTOSAMINIDASE FOR INFLUENZA

[76] Inventor: Nobuto Yamamoto, 1040 66th Ave., Philadelphia, Pa. 19126

[21] Appl. No.: 938,553

[22] Filed: Sep. 26, 1997

Related U.S. Application Data

[63] Continuation-in-part of Ser. No. 779,729, Jan. 6, 1997, Pat. No. 5,712,104, which is a continuation-in-part of Ser. No. 618,485, Mar. 19, 1996, abandoned.

[51] Int. Cl.$^6$ .................................................. C12Q 1/70
[52] U.S. Cl. .................. 435/5; 435/7.9; 435/18; 435/34; 436/531
[58] Field of Search ................... 435/5, 7.1, 7.23, 435/7.9, 7.92, 7.94, 18, 34; 436/501, 531, 813, 518

*Primary Examiner*—Jeffrey Stucker
*Attorney, Agent, or Firm*—Caesar, Rivise, Bernstein, Cohen & Pokotilow, Ltd.

[57] ABSTRACT

Influenza virus-infected cells secrete α-N-acetylgalactosaminidase into the blood stream, resulting in the deglycosylation of the Gc protein. This inactivates the MAF precursor activity of the Gc protein, leading to immunosuppression. Thus, the α-N-acetylgalactosaminidase activity in a patient's bloodstream can serve as a diagnostic and prognostic index. Antibody-sandwich ELISA method and kits for influenza virus specific α-N-acetylgalactosaminidase as an antigen were developed to detect serum or plasma α-N-acetylgalactosaminidase activity in influenza infected patients and are used as a diagnostic/prognostic index.

2 Claims, 3 Drawing Sheets

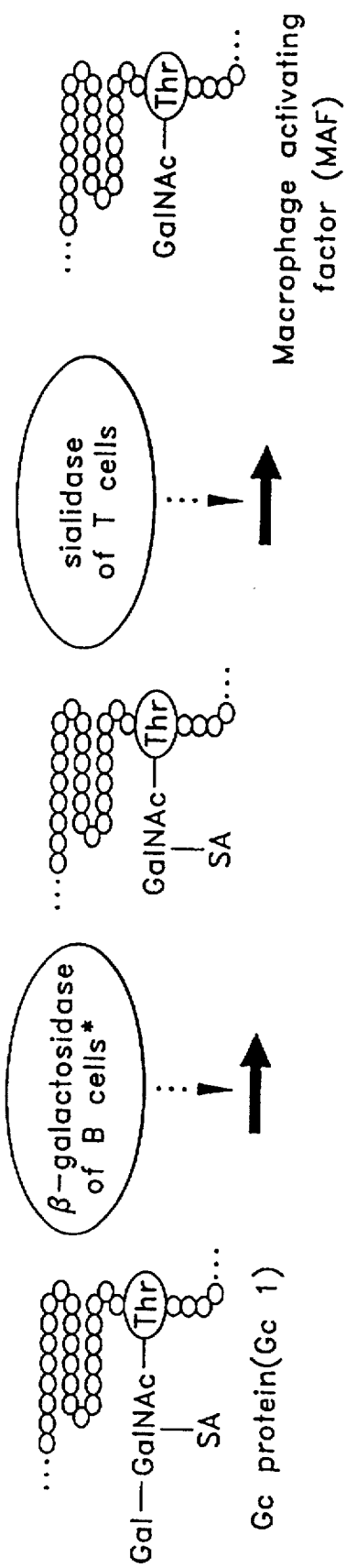
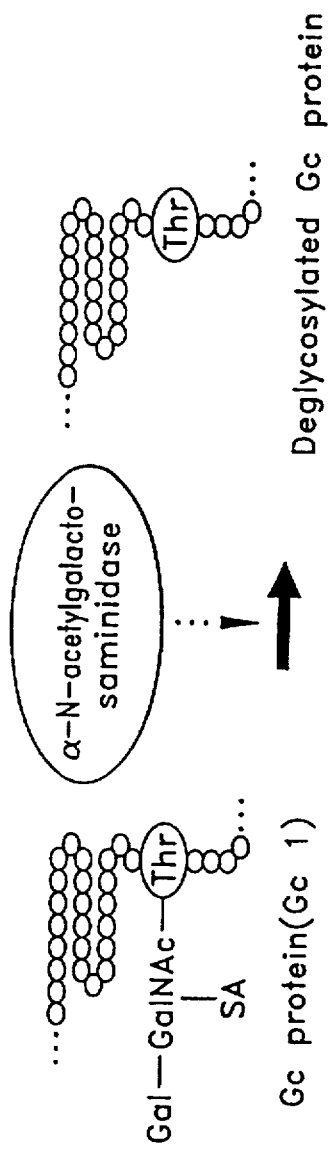
FIG. 1A
FIG. 1B

DIAGNOSTIC AND PROGNOSTIC ELISA ASSAYS OF SERUM α-N-ACETYLGALACTOSAMINIDASE FOR INFLUENZA

RELATED APPLICATIONS

This application is a continuation-in-part application of application Ser. No. 08/779,729 filed Jan. 6, 1997, now U.S. Pat. No. 5,712,104, which is a continuation-in-part of application Ser. No. 08/618,485 filed Mar. 19, 1996, now abandoned, the entire disclosures of which are incorporated by reference herein.

FIELD OF THE INVENTION

This invention relates to diagnostic and prognostic methods utilizing AN enzyme-linked immunosorbent assay (ELISA) to detect the specific enzyme, α-N-acetylgalactosaminidase that causes immunosuppression, found in the blood stream of AIDS/HIV-infected and influenza patients.

TABLE OF TERMS

| | |
|---|---|
| Gc protein | Vitamin $D_3$-binding protein |
| MAF | macrophage activating factor |
| GcMAF | Gc protein-derived macrophage activating protein |
| PBMC | peripheral blood mononuclear cells |
| HA | hemagglutinin |
| Nag | α-N-acetylgalactosaminidase |
| NagAg | α-N-acetylgalactosaminidase as an antigen |
| ELISA | enzyme-linked immunosorbent assay |

SUMMARY OF THE INVENTION

Vitamin $D_3$-binding protein (Gc protein) is the precursor for macrophage activating factor (MAF). HIV- and influenza virus-infected cells secrete α-N-acetylgalactosaminidase into the blood stream, resulting in the deglycosylation of Gc protein. This inactivates the MAF precursor activity of the Gc protein, leading to immunosuppression. Thus, α-N-acetylgalactosaminidase activity in a patient's blood stream can serve as a diagnostic and prognostic index. An antibody-sandwich ELISA method and kits for HIV and influenza specific α-N-acetylgalactosaminidase as antigens were developed to detect serum or plasma α-N-acetylgalactosaminidase in AIDS/HIV-infected and influenza patients and used as a diagnostic/prognostic index.

DESCRIPTION OF THE DRAWINGS

Other objects and many attendant features of this invention will become readily appreciated as the same becomes better understood by reference to the following detailed description when considered in connection with the accompanying drawings wherein:

FIG. 1A is a schematic illustration of the conversion of Gc protein to macrophage activating factor (MAF).

FIG. 1B is a schematic illustration of the deglycosylation of Gc protein in HIV- or influenza-infected patient's blood stream.

BACKGROUND OF THE INVENTION

Figure 2:
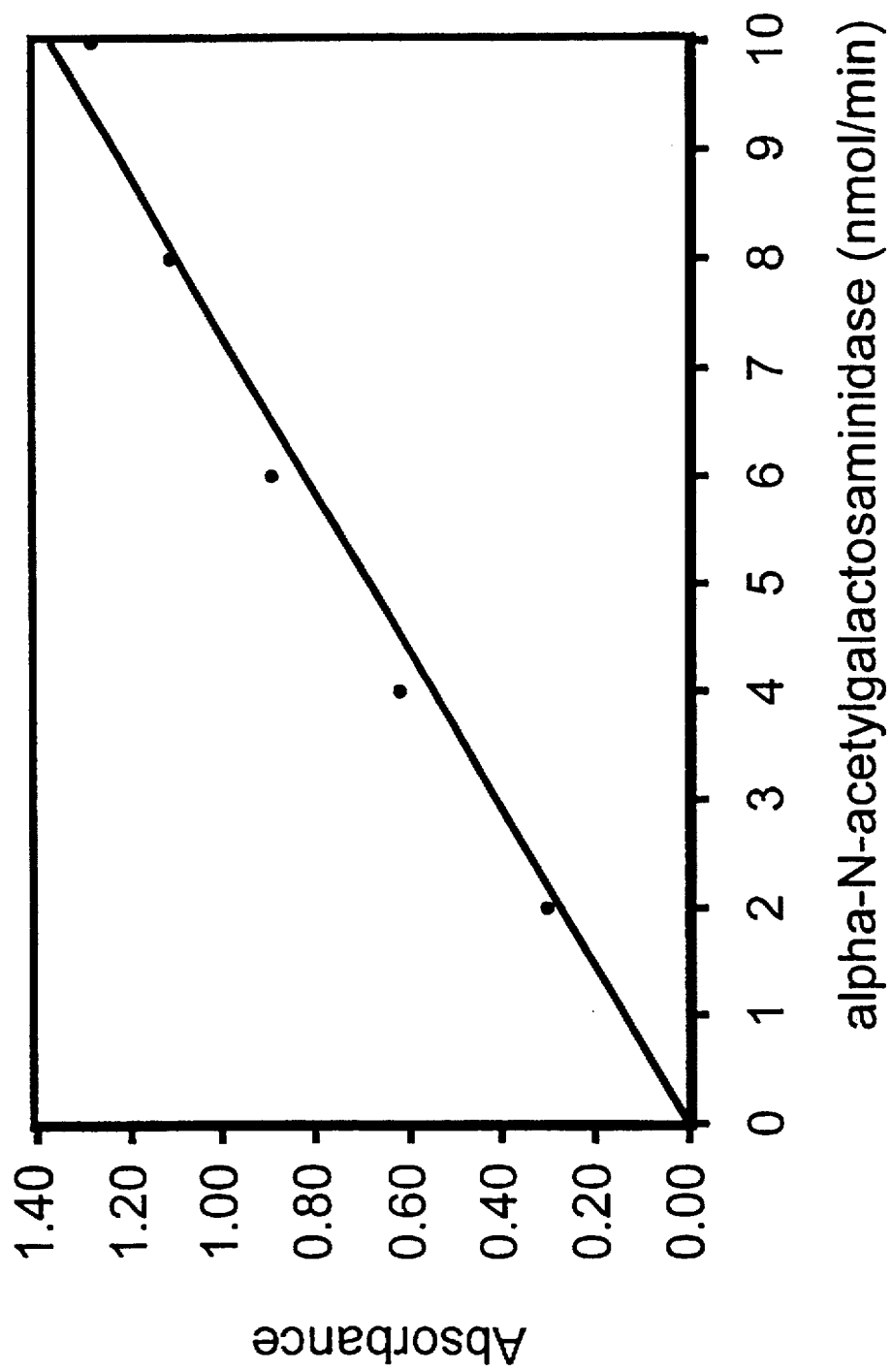
FIG. 2 shows the standard correlation between α-N-acetylgalactosaminidase as a HIV-antigen and absorbance (color density) for alkaline phosphatase activity of ELISA.

A. Immunosuppression Resulted from Loss of MAF Precursor Activity

Infections result in inflammation which attracts and activates macrophages. Inflamed lesions release lysophospholipids. Administration into mice of small doses (5–20 µg/mouse) of lysophosphatidylcholine (lyso-Pc) and other lysophospholipids resulted in the greatly enhanced phagocytic and superoxide generating capacities of macrophages (Ngwenya and Yamamoto, Proc. Soc. Exp. Biol. Med. 193: 118, 1990; Yamamoto et al., Inf. Imm. 61: 5388, 1993; Yamamoto et al., Inflammation. 18: 311, 1994). The inflammation-primed macrophage activation process is the major macrophage activation cascade (Yamamoto, Mol. Immunol. 33: 1157, 1996), which requires the participation of B and T lymphocytes and serum vitamin D binding protein (DBP; human DBP is known as group specific components or Gc protein). The inducible β-galactosidase ($Bgl_i$) of inflammation-primed (or lyso-Pc-treated) B cells and the Neu-1 sialidase of T cells convert Gc glycoprotein to the macrophage activating factor (MAF), a protein with N-acetylgalactosamine as the remaining sugar moiety (FIG. 1) (Yamamoto and Homma, Pro. Natl. Acad. Sci. USA. 88: 8539, 1991; Yamamoto, Mol. Immunol. 33: 1157, 1996). Thus, the Gc protein is a precursor for MAF. Incubation of Gc protein with immobilized β-galactosidase and sialidase generates a remarkably high titered MAF (termed GcMAF) (Yamamoto, Mol. Immunol. 33: 1157, 1996; Yamamoto and Kumashiro, J. Immunol. 151: 2794, 1993; Naraparaju and Yamamoto, Immunol. Lett. 43: 143, 1994; U.S. Pat. Nos. 5,177,002 and 5,326,749). Administration of a minute amount (10 pg/mouse; 100 ng/human) of GcMAF resulted in greatly enhanced phagocytic and superoxide generating capacities of macrophages.

When peripheral blood monocytes/macrophages (phagocytes) of over 250 HIV-infected patients were treated with a small amount (100 pg/ml) of GcMAF, the phagocytes of all patients were activated for generating more than 4.0 nmoles of superoxide/min/$10^6$ phagocytes as with healthy humans. When a mixture of lymphocytes and phagocytes was treated with 1 µg lyso-Pc/ml for 30 minutes and cultured in a medium supplemented with Gc protein (1 ng/ml) for 3 h, the phagocytes of all patients were activated for generating more than 4.0 nmoles of superoxide/min/$10^6$ phagocytes. The results indicate that lymphocytes of these patients are capable of converting Gc protein to MAF. However, when a mixture of lyso-Pc-treated lymphocytes and phagocytes was cultured in a medium supplemented with patient own serum (0.1%) as a source of Gc protein for 3 hours, the phagocytes were not activated with patient serum of about 10% of this patient population and produced less than 0.7 nmoles of superoxide/min/$10^6$ phagocytes (Yamamoto et al., AIDS Res. Human Retro. 11: 1373, 1995). These patients having severely decreased precursor activity of serum Gc protein were found to be approximately ¼ of the AIDS patients. However, electrophoretic analysis showed no detectable change in either quantity or molecular weight of plasma Gc protein. Thus, the lost or reduced precursor activity of a patient's Gc protein is due to the deglycosylation of the Gc protein (Yamamoto et al., AIDS Res. Human Retro. 11: 1373, 1995). Deglycosylated Gc protein cannot be converted to MAF (FIG. 1b). Therefore, macrophage activation cannot develop in certain AIDS/HIV-infected patients. Since macrophage activation for phagocytosis and antigen presentation is the first step in the immune development cascade, the patients incapable of macrophage activation become severely immunosuppressed. This may explain why AIDS patients die from overwhelming opportunistic infection. The MAF precursor activity of Gc protein in the sera of approximately 25% of this patient population was moderately reduced (ranging from 1.6–3.6 nmoles of superoxide produced/min/$10^6$ phagocytes). The remaining asymptomatic (65%) HIV-infected patients had MAF precursor activities similar to those of healthy humans.

All HIV-infected patient's sera were found to contain α-N-acetylgalactosaminidase that deglycosylates Gc protein (Yamamoto et al., AIDS Res. Human Retro. 11: 1373, 1995). Patients having severely decreased precursor activity carry high serum α-N-acetylgalactosaminidase activity whereas the asymptomatic patients having high precursor activity carry a very low level of serum α-N-acetylgalactosaminidase activity. Thus, plasma α-N-acetylgalactosaminidase activity has an inverse correlation with the MAF precursor activity of Gc protein (Yamamoto et al., AIDS Res. Human Retro. 11: 1373, 1995).

Similarly, an influenza patient's precursor activity is lost or decreased because serum Gc protein is deglycosylated by α-N-acetylgalactosaminidase found in the blood stream of influenza patients. Since the deglycosylated Gc protein cannot be converted to MAF, the lack of macrophage activation in influenza patients leads to immunosuppression, which causes the secondary bacterial infections (i.e., pneumonia).

In my prior three U.S. Pat. Nos. 5,177,002, 5,326,749, and 5,620,846, the entire disclosures of which are incorporated by reference herein, as are my above cited journal articles, is disclosed the macrophage activating factor, processes for preparing them as well as methods of inducing macrophage activation in a person in need of such activation, and diagnostic or prognostic assays of serum α-N-acetylgalactosaminidase in cancer and AIDS patients.

B. The Origin of α-N-acetylgalactosaminidase

Serum α-N-acetylgalactosaminidase activity was found in the blood stream of all stages of HIV-infected patients but not in healthy humans (Yamamoto et al., AIDS Res. Human Retro. 11: 1373, 1995). In contrast, serum β-N-acetylglucosaminidase activity levels of healthy humans are equivalent to those of HIV-infected patients. Thus, serum β-N-acetylglucosaminidase seems to be clinically insignificant. In fact, α-N-acetylgalactosaminidase activity is responsible for the deglycosylation of Gc protein because the Gc protein is O-glycosylated (Yamamoto et al., AIDS Res. Human Retro. 11: 1373, 1995).

The deglycosylation of Gc protein by serum α-N-acetylgalactosaminidase appears to be the major cause for immunosuppression in AIDS/HIV-infected patients. Cultured HIV-infected cells can secrete α-N-acetylgalactosaminidase into culture medium. When peripheral blood mononuclear cells (PBMC) of HIV-infected patients were cultured for 3 days, small amounts of α-N-acetylgalactosaminidase were detected in the culture media. If these PBMC were treated with mitomycin C (5 μg/ml) or BUDR as a provirus inducer (Sato et al., Arch. Virol. 54: 333, 1977) for 30 min and cultured for 3 days, α-N-acetylgalactosaminidase enzyme activity in culture media increased significantly. This enzyme is immunoprecipitable with polyclonal anti-HIV antibody, indicating that this enzyme is a viral gene product. Moreover, serum α-N-acetylgalactosaminidase of HIV-infected patients was immunoprecipitable without addition of anti-HIV antibody, suggesting that the enzyme is already complexed with patient own immunoglobulin G. The immunogenicity of the serum enzyme also suggests that the serum enzyme is likely to be coded by a viral gene. In fact, the HIV-envelope protein, gp120, was found to contain α-N-acetylgalactosaminidase activity.

Similarly, all influenza infected patient's sera contain α-N-acetylgalactosaminidase. An influenza virus envelope protein, hemagglutinin (HA), was found to contain α-N-acetylgalactosaminidase activity. Influenza virus-infected cells can secrete this enzyme as unassembled HA protein and its fragments into the blood stream, resulting in the deglycosylation of Gc protein. The deglycosylated Gc protein cannot be converted to MAF. Thus, lack of macrophage activation in influenza patients leads to immunosuppression, which frequently causes the secondary bacterial infections (i.e., pneumonia). Since the serum α-N-acetylgalactosaminidase of influenza patients was found to be a viral coded product and resides on the HA protein, the α-N-acetylgalactosaminidase activity in a patient's bloodstream appears to be indicative of virus load and can serve as a diagnostic and prognostic index for these influenza patients.

All viral components in HIV and influenza are antigenically distinct, serum α-N-acetylgalactosaminidase activities as the diagnostic/prognostic indices of these patients are antigenically distinguishable among these individual viral diseases. Thus, ELISA for these viral enzymes should be valuable for diagnosis and prognosis of these diseases.

C. Diagnostic and Prognostic Significance of α-N-Acetylgalactosaminidase Activity in Blood Stream of AIDS/HIV-infected and Influenza Patients 1. Assay protocol for detection of α-N-acetylgalactosaminidase in blood stream of AIDS/HIV-infected and influenza patients i) Schematic illustration.

Detection procedure for deglycosylating enzyme of serum Gc protein, α-N-acetylgalactosaminidase, in AIDS/HIV-infected and influenza patient's blood stream.

Step. I. Stepwise 30 and 70% ammonium sulfate precipitation of plasma or serum: Serum/plasma (1 ml)+30% and then 70% saturated ammonium sulfate 70% precipitate→dissolved in 50 mM citrate phosphate buffer (pH 6.0)→dialyzed against the same buffer at 4° C. for overnight. The dialysates was made up to 1 ml in volume.

Step. II. Enzyme assay of α-N-acetylgalactosaminidase

Reaction mixture: 250 μl of the dialyzed sample+250 ml of 50 mM citrate phosphate buffer (pH 6.0) containing 5 μmoles of p-nitrophenyl N-acetyl-α-D-galactosaminide as substrate.

Incubation time: 60 min, terminated by adding 200 μl of 10% TCA. After centrifugation of the reaction mixture, 300 μl of 0.5M $Na_2CO_3$ was added to the supernatant.

Activity measurement: absorbance of amount of released p-nitrophenol was determined spectrophotometrically at 420 nm with Beckman DU 600 Spectrop hotometer and expressed as specific activity unit of nmole/mg/min. Protein concentrations were determined by the Bradford method.

ii) Descriptive enzyme assay procedure for α-N-acetylgalactosaminidase.

Plasma/serum (1 ml) of patients was precipitated with 70% saturated ammonium sulfate. The ammonium sulfate precipitate was dissolved in 50 mM citrate phosphate buffer (pH 6.0) and dialyzed against the same buffer at 4° C. The volume of the dialysate was made up to 1 ml. Ammonium sulfate precipitation also separates the enzyme from product inhibitors. The substrate solution (250 µl) contained 5 µmoles of p-nitrophenyl N-acetyl-α-D-galactosaminide in a 50 mM citrate phosphate buffer (pH 6.0). The reaction was initiated by addition of 250 µl of the dialyzed samples, kept at 37° C. for 60 min and terminated by adding 200 µl of 10% TCA. After centrifugation of the reaction mixture, 300 µl of 0.5M $Na_2CO_3$ solution was added to the supernatant. The amount of released p-nitrophenol was determined spectrophotometrically at 420 nm with a Beckman DU 600 Spectrophotometer and expressed as specific activity unit of nmole/mg/min. Protein concentration were estimated by Bradford method (Bradford, *Anal Biochem* 72: 248, 1976).

2. Diagnostic/Prognostic Utility of Serum α-N-acetylgalactosaminidase for Patient infected with HIV or Influenza.

Serum α-N-acetylgalactosaminidase activity assesses infected viral load because the serum enzyme level is proportional to the total amount of unassembled viral envelope components (i.e., gp120 for HIV and HA for influenza), which is indicative of viral load.

a) HIV Infection.

As shown in Table 1, serum α-N-acetylgalactosaminidase activity of the first 14 patients out of 250 patients represents a diagnostic index which shows inverse correlation with the MAF precursor activity of Gc protein but no obvious correlation with $CD4^+$ values (Yamamoto et al., *AIDS Res. Human Retro.* 11: 1373, 1995).

b) Influenza virus infection.

As shown in Table 2, serum α-N-acetylgalactosaminidase activity of 12 influenza patients represents diagnostic index that shows an inverse correlation with the MAF precursor activity of their serum Gc protein.

DESCRIPTION OF THE INVENTION

Description of the Enzyme-Linked Immunosorbent (ELISA) Assay Procedure for α-N-acetylgalactosaminidase Activity as an Antigen in Blood Stream of AIDS/HIV-Infected and Influenza Patients In the immunoassay procedure for the detection of serum or plasma α-N-acetylgalactosaminidase (Nag) as an antigen (NagAg), antibody-sandwich ELISA kits were prepared.

1. Preparation of antibody. The viral Nag enzyme was purified from sera of HIV-infected patients or embryonated chicken egg grown influenza virus-lysates (excluding complete virions) and used for immunization of animals (rabbit, goat and mouse). Polyclomal antibodies (goat and rabbit) and monoclonal antibodies against α-N-acetylgalactosaminidase (NagAg) were prepared. An immunoglobulin fraction was purified from antisera or monoclonal ascites fluid using ammonium sulfate (50% saturated) fractionation and DE52 ionic exchange column with 10 mM PBS (0.15M NaCl and 10 mM phosphate buffer) or protein A columns.

2. Conjugation of alkaline phosphatase to antibodies. Dialyze 5 mg/ml monoclonal or polyclonal antibody solution in 0.1M phosphate buffer at pH 6.8 (PBS) overnight at 4° C. Add 0.5 mg of dialyzed antibody to 1.5 mg of alkaline phosphatase (immunoassay grade; Boehringer Mannheim, Indianapolis, Ind.) in 10 ml of 10 mM PBS. Add 80 µl 25% glutaraldehyde and mix gently. Let stand at room temperature for 2 hrs. Stop reaction by adding an equivalent volume (10 ml) of PBSLE (10 mM PBS containing 100 mM lysine and 100 mM ethanolamine). Desalt with Sephadex G25 column in PBSN (10 mM PBS with 0.05M $NaN_3$). Mix 20 ml of alkaline phosphatase-antibody conjugates with 40 ml of blocking buffer (0.17M borate buffer containing 2.5 mM $MgCl_2$, 0.05% Tween 20, 1 mM EDTA, 0.25% BSA and 0.05% $NaN_3$). Filter 60 ml of the conjugates through a low-protein binding filter, Millex HV 0.45 µm (Millipore Corp. Bedford, Mass.), for sterilization and store at 4° C.

3. Preparation of antibody coated microtiter plates. Using multichannel pipets and tips, dispense 50 µl of polyclonal or monoclonal antibody solution 2 µg/ml in PBSN into each well of a microtiter plate (microwell). Wrap the plates in plastic wrap to seal and incubate 2 hrs at 37° C. or overnight at room temperature. Rinse the antibody coated plate by flooding with distilled water more than three times. Fill each well with blocking buffer dispensed as a stream from a bottle and incubate 30 min at room temperature. Rinse the plate three times with distilled water and remove any residual liquid by gently flicking it face down onto paper towels.

4. Antigen (NagAg) preparation for ELISA.

a) Standard antigen for standard curve. Prepare a standard antigen-dilution series by successive dilutions of NagAg stock (e.g., the enzyme purified from AIDS patient sera or embryonated chicken egg-grown influenza virus lysates, excluding complete virions) in blocking buffer. The activity range of Nag enzyme dilution spans from 2 to 10 nmole/min, corresponding to NagAg antigens dilution ranging from 12 to 60 µg/ml.

b) Test sample. Serum or plasma of HIV-infected and influenza patients.

5. ELISA.

Step I. Add 50-µl aliquots of 1/10 serum dilution in PBSN of the test NagAg sample solutions (patient serum or plasma enzyme) or the standard NagAg (enzyme) dilutions to the antibody coated wells and incubate 2 hrs at room temperature. Rinse plate three times in distilled water. Fill each well with blocking buffer and incubate 10 min at room temperature. Rinse three times with water and remove residual liquid.

Step II. Add 50 µl specific antibody-alkaline phosphatase conjugate (300 ng/ml) and incubate 2 hrs at room temperature. Wash plate as in Step I.

Step III. Add 75 µl of p-nitrophenyl phosphate (NPP) substrate solution (4 µmoles/ml) to each well and incubate for 1 hr at room temperature. Alkaline phosphatase activity causes the solution to change color. Color density (absorbance) relates to the amount of NagAg. Read the plate on a microtiter plate reader with a 405-nm filter.

Figure 3:
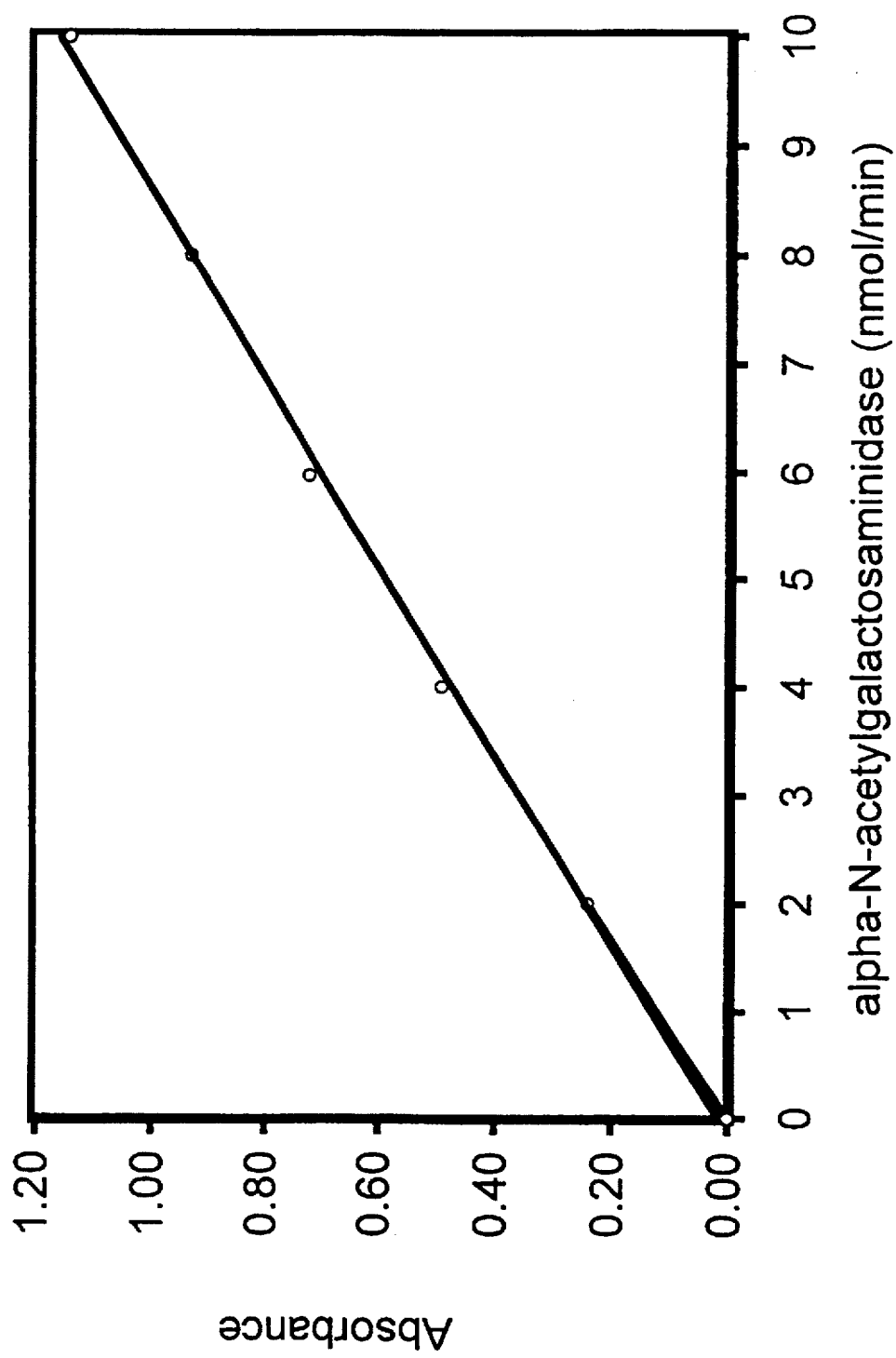
FIG. 3 shows the standard correlation between α-N-acetylgalactosaminidase as an influenza-antigen and absorbance (color density) for alkaline phosphatase activity of ELISA.

6. Data analysis. Standard curves were constructed for the ELISA produced by the dilutions of the standard antigen (NagAg) of purified HIV- and influenza-enzymes. The NagAg concentrations were expressed as Nag enzyme activities and plotted on the x axis and absorbance (color density) of alkaline phosphatase activity on the y axis, as shown in FIG. 2 for HIV and FIG. 3 for influenza virus. Interpolate the absorbance of the test patient serum/plasma sample to determine α-N-acetylgalactosaminidase activity. Table 3 exemplifies the patient enzyme activities determined from ELISA for sera of 16 AIDS/HIV-infected patients. Similar results were also observed with 14 influenza patients as shown in Table 4.

Since antibodies to HIV and influenza virus enzymes are specific to the respective enzymes (NagAg) and do not cross-react, this antibody sandwich ELISA distinguishes individual enzymes. Thus, the present method is particularly useful if these patients are dually infected (e.g., influenza virus infection of AIDS/HIV-infected patients).

TABLE 1

Serum α-N-acetylgalactosaminidase activity detected in HIV-infected patient plasma and its correlation with the precursor activity of plasma Gc protein and the CD4+ value.

| Patient No. | α-N-acetylgalactosaminidase Specific activity (nmoles/mg/min) | Disease stage indices | |
|---|---|---|---|
| | | Precursor activity | CD4+ value |
| 1 | 13.12 | 0.54 | 188 |
| 2 | 2.51 | 3.42 | 102 |
| 3 | 12.80 | 0.69 | 136 |
| 4 | 1.43 | 4.43 | 577 |
| 5 | 0.51 | 5.14 | 160 |
| 6 | 0.54 | 5.22 | 222 |
| 7 | 1.01 | 4.52 | 298 |
| 8 | 0.81 | 5.03 | 156 |
| 9 | 2.63 | 3.14 | 849 |
| 10 | 3.15 | 2.91 | 22 |
| 11 | 2.28 | 3.62 | 585 |
| 12 | 3.03 | 2.91 | 845 |
| 13 | 3.54 | 1.64 | 326 |
| 14 | 1.35 | 4.63 | 305 |
| Control[a] | 0.24[b] | 5.10 | — |

[a]Average of 5 healthy humans. [b]This enzyme activity in healthy humans was found to be α-galactosidase.

TABLE 2

Precursor activity of Gc protein and α-N-acetylgalactosaminidase activities detected in blood stream of acute influenza patients.

| Patient (No) | α-N-acetylgalactosaminidase Specific activity (nmole/min/mg) | Precursor activity Superoxide produced (nmole/min/10[6] cells) |
|---|---|---|
| 1 | 1.96 | 3.01 |
| 2 | 1.75 | 3.27 |
| 3 | 4.11 | 1.95 |
| 4 | 1.68 | 3.45 |
| 5 | 1.53 | 4.89 |
| 6 | 0.87 | 4.39 |
| 7 | 2.23 | 2.54 |
| 8 | 5.93 | 1.26 |
| 9 | 3.65 | 2.17 |
| 10 | 2.23 | 2.65 |
| 11 | 1.68 | 4.70 |
| 12 | 2.83 | 2.33 |
| Control | 0.29* | 5.86 |

*This enzyme activity in healthy humans was found to be α-galactosidase.

TABLE 3

Serum α-N-acetylgalactosaminidase activity of AIDS/HIV-infected patients determined from ELISA

| Patient No | Absorbance (Color density) | α-N-acetylgalactoeaminidase activity (nmole/mg/min) |
|---|---|---|
| 1 | 0.325 | 2.37 |
| 2 | 0.498 | 3.64 |
| 3 | 0.996 | 7.28 |
| 4 | 0.238 | 1.74 |
| 5 | 0.429 | 3.13 |
| 6 | 1.213 | 8.87 |
| 7 | 0.592 | 5.32 |
| 8 | 1.370 | 10.01 |
| 9 | 0.254 | 1.86 |
| 10 | 0.587 | 4.29 |
| 11 | 0.272 | 1.98 |
| 12 | 0.622 | 4.55 |
| 13 | 0.712 | 3.20 |
| 14 | 0.232 | 1.69 |
| 15 | 0.281 | 2.05 |
| 16 | 0.185 | 1.35 |

TABLE 4

Serum α-N-acetylgalactosaminidase activity of influenza virus-infected patients determined from ELISA.

| Patient No | Absorbance (Color density) | α-N-acetylgalactoeaminidase activity (nmole/mg/min) |
|---|---|---|
| 1 | 0.188 | 1.64 |
| 2 | 0.455 | 3.97 |
| 3 | 0.172 | 1.50 |
| 4 | 0.530 | 4.63 |
| 5 | 0.222 | 1.94 |
| 6 | 0.324 | 2.83 |
| 7 | 0.203 | 1.77 |
| 8 | 0.215 | 1.88 |
| 9 | 0.418 | 3.65 |
| 10 | 0.242 | 2.11 |
| 11 | 0.318 | 2.78 |
| 12 | 0.225 | 1.96 |
| 13 | 0.198 | 1.73 |
| 14 | 0.218 | 1.85 |

REFERENCES CITED

The following references are cited and their entire text is incorporated fully herein as are all references set forth above in the specification.

U.S. PATENT DOCUMENTS

U.S. Pat. Nos. 5,177,002, 5,326,749 and 5,620,846 (Yamamoto).

OTHER PUBLICATIONS

1. Bradford, M. M., A rapid and sensitive method for the quantitation of microgram quantities of protein utilizing the principle of protein-dye binding. Anal. Biochem. 72: 248–254 (1976).
2. Sato, M., Tanaka, H., Yamada, T. and Yamamoto, N., Persistent infection of BHK/WI-2 cells with rubella virus and characterization of rubella variants. Arch. Virology 54: 333–343 (1977).
3. Ngwenya, B. Z. and Yamamoto, N., Contribution of lysophosphatidylcholine treated nonadherent cells to mechanism of macrophage stimulation. Proc. Soc. Exp. Biol. Med. 193: 118–124 (1990).
4. Yamamoto, N. and Homma, S., Vitamin $D_3$ binding protein (group-specific component, Gc) is a precursor for the macrophage activating signal from lysophosphatidylcholine-treated lymphocytes. Proc. Natl. Acad. Sci. USA. 88: 8539–8543 (1991).
5. Yamamoto, N. and Kumashiro, R., Conversion of vitamin $D_3$ binding protein (Group-specific component) to a macrophage activating factor by stepwise action of β-galactosidase of B cells and sialidase of T cells. J. Immunol. 151: 2794–2902 (1993).
6. Yamamoto, N., Kumashiro, R., Yamamoto, M., Willett, N. P. and Lindsay, D. D., Regulation of inflammation-primed activation of macrophages by two serum factors, vitamin $D_3$-binding protein and albumin. Inf. Imm. 61: 5388–5391 (1993).

7. Yamamoto, N., Willett, N. P. and Lindsay, D. D., Participation of serum proteins in the inflammation-primed activation of macrophages. Inflammation. 18: 311–322 (1994).

8. Naraparaju, V. R. and Yamamoto, N., Roles of β-galactosidase of B lymphocytes and sialidase of T lymphocytes in inflammation-primed activation of macrophages. Immunol. Lett. 43: 143–148 (1994).

9. Yamamoto, N., Naraparaju, V. R. and Srinivasula, S. M., Structural modification of serum vitamin $D_3$-binding protein and immunosuppression in HIV-infected patients. AIDS Res. Human Ret. 11: 1373–1378 (1995).

10. Yamamoto N. Structural definition of a potent macrophage activating factor derived from vitamin $D_3$ binding protein with adjuvant activity for antibody production. Molecular Immunol. 33: 1157–1164 (1996).

I claim:

1. A method for detecting α-N-acetylgalactosaminidase in plasma or serum to screen for influenza comprising the steps of:

(a) providing polyclonal or monoclonal antibodies against influenza virus α-N-acetylgalactosaminidase;

(b) providing a microtiter plate coated with the antibodies;

(c) adding the serum or plasma to the microtiter plate;

(d) providing alkaline phosphatase-antibody conjugates reactive with influenza virus α-N-acetylgalactosaminidase to the microtiter plate;

(e) providing p-nitrophenyl-phosphate to the microtiter plate; and (f) comparing the reaction which occurs as a result of steps (a) to (e) with a standard curve to determine the level of influenza virus α-N-acetylgalactosaminidase compared to a normal individual.

2. An antibody-sandwich ELISA kit to screen for influenza infection by detecting influenza virus α-N-acetylgalactosaminidase in plasma or serum, the kit comprising:

(a) a microtiter plate coated with polyclonal or monoclonal antibodies specific to influenza virus α-N-acetylgalactosaminidase;

(b) polyclonal or monoclonal antibody-alkaline phosphatase conjugates reactive with influenza virus α-N-acetylgalactosaminidase;

(c) p-nitrophenyl-phosphate; and (d) influenza virus α-N-acetylgalactosaminidase as an antigen standard.

\* \* \* \* \*